United States Patent [19]

Guy et al.

[11] Patent Number: 5,171,546

[45] Date of Patent: Dec. 15, 1992

[54] USE OF THIOETHER LIGANDS FOR SEPARATING PALLADIUM FROM AQUEOUS SOLUTIONS AND IN PARTICULAR NITRIC SOLUTIONS FOR DISSOLVING IRRADIATED NUCLEAR FUEL ELEMENTS

[75] Inventors: Alain Guy, Pontcarre; Marc Lemaire, Villeurbanne; Jacques Foos, Orsay; Gérard Le Buzit, Crosne; Vincent Guyon, Paris; Thierry Moutarde, Piolenc; Rodolph Chomel, Camaret-sur-Aigues; Micheline Draye, Challes-les-Eaux, all of France

[73] Assignee: Cogema-Compagnie Generale des Matieres Nucleaires, Velizy Vallacoublay, France

[21] Appl. No.: 699,756

[22] Filed: May 14, 1991

[30] Foreign Application Priority Data

May 15, 1990 [FR] France .................. 90 06041

[51] Int. Cl.$^5$ .............................. B01D 11/00
[52] U.S. Cl. ................................ 423/8; 423/22; 252/627; 534/10
[58] Field of Search ............... 423/22, 2, 8; 534/10; 252/627

[56] References Cited

U.S. PATENT DOCUMENTS

| | | | |
|---|---|---|---|
| 2,519,586 | 8/1950 | McCaulay et al. | 260/609 |
| 3,242,135 | 3/1966 | Bown et al. | 260/48.85 |
| 3,293,209 | 12/1966 | Baldwin et al. | 260/45.95 |
| 3,315,000 | 4/1967 | Ransley | 260/609 |
| 3,745,206 | 7/1973 | Haluska et al. | 423/22 |
| 3,985,552 | 10/1976 | Edwards | 75/426 |
| 4,021,246 | 5/1977 | Bachman et al. | 96/67 |
| 4,162,231 | 7/1979 | Horwitz et al. | 252/627 |
| 4,479,822 | 10/1984 | Haynes et al. | 423/22 |

FOREIGN PATENT DOCUMENTS

| 177784 | 10/1985 | European Pat. Off. . |
|---|---|---|
| 2514318 | 10/1971 | Fed. Rep. of Germany . |
| 966929 | 8/1964 | United Kingdom . |

OTHER PUBLICATIONS

Chemical Abstracts, vol. 72, No. 16, 1970, p. 32, Abstract No. 79858d.

(List continued on next page.)

*Primary Examiner*—Brooks H. Hunt
*Assistant Examiner*—Ngoclan T. Mai
*Attorney, Agent, or Firm*—Pearne, Gordon, McCoy & Granger

[57] ABSTRACT

The invention relates to the use of thioether ligands in accordance with the formula:

$$\begin{array}{l} CH_2-S-R^1 \\ | \\ A \\ | \\ CH_2-S-R^2 \end{array} \quad (I)$$

or $$\begin{array}{l} R^3-CH-S-R^1, \\ | \\ R^3-CH-S-R^2 \end{array} \quad (II)$$

in which $R^1$ and $R^2$, which can be the same or different, represent alkyl radicals, $R^3$ is an alkyl radical and A represents a divalent radical chosen from among the radicals of formula:

$$-(CH_2)_m-$$

$$-(CH_2)_n-X-(CH_2)_p-$$

$$\begin{array}{l} -CH- \\ | \\ R^3 \end{array}$$

in which m is equal to 0 or is an integer from 1 to 6, n and p are integers between 1 and 6 and X represents O or S, for recovering the palladium present in a nitric aqueous solution ($A_0$) for dissolving irradiated nuclear fuel elements.

For example, it is possible to use the ligand of formula (I) with A representing $CH_2-S-CH_2$ and $R^1$ and $R^2$ representing $C_{10}H_{21}$.

11 Claims, 2 Drawing Sheets

OTHER PUBLICATIONS

Chemical Abstracts, vol. 85, No. 19, 1976, p. 481, Abstract No. 142536h.
Chemical Abstracts, vol. 58, No. 7, 1963, Abstract No. 6684d.
Chemical Abstracts, vol. 85, No. 19, 1976, p. 481, Abstract No. 142531c.
Synthesis, No. 9, Sep. 1987, pp. 841–843.
Journal of Inorganic and Nuclear Chemistry, vol. 42, No. 6, 1980.

USE OF THIOETHER LIGANDS FOR SEPARATING PALLADIUM FROM AQUEOUS SOLUTIONS AND IN PARTICULAR NITRIC SOLUTIONS FOR DISSOLVING IRRADIATED NUCLEAR FUEL ELEMENTS

The present invention relates to the use of thioether ligands, which are non-cyclic thioethers or podands, for separating palladium from aqueous solutions. It more specifically relates to thioether ligands able to selectively separate palladium from an aqueous solution for the reprocessing of irradiated nuclear fuels.

For a number of years the most widely used procedure for reprocessing irradiated nuclear fuels has consisted of dissolving the fuel in a nitric solution, which leads to the obtaining of a nitric aqueous solution containing uranium, plutonium and fission products. Following this dissolving stage, the thus obtained nitric aqueous solution is contacted with an organic solvent for extracting therein the uranium and the plutonium and for separating them from most of the fission products. This is followed by the reextraction of the uranium and the plutonium in an aqueous phase and the separation of the uranium from the plutonium present in said aqueous phase by means of an organic solvent.

Among the fission products present in the nitric aqueous dissolving solution, palladium occurs in a non-negligible concentration, which it would be advantageous to recover at this stage. However, for separating palladium from said solution, it is necessary to have a means making it possible to selectively extract the palladium in the presence of numerous elements, including uranium and plutonium present in said solution at much larger concentrations than the palladium.

The present invention specifically relates to a process for separating the palladium present in an aqueous solution by means of thioether ligands, which are selective extractants of palladium, which have a good stability under irradiation and which make it possible to quantitatively separate the palladium from a dissolving solution for irradiated nuclear fuels.

According to the invention, this process comprises the following stages:

a) contacting the aqueous solution containing the palladium with an organic extractant constituted by a thioether in accordance with the formula:

$$\begin{array}{c} CH_2-S-R^1 \\ | \\ A \\ | \\ CH_2-S-R^2 \end{array} \quad (I)$$

or $$\begin{array}{c} R^3-CH-S-R^1 \\ | \\ R^3-CH-S-R^2 \end{array} \quad (II)$$

or incorporating a radical of formula:

$$\begin{array}{c} CH_2-S-R^1 \\ | \\ A \\ | \\ CH_2-S- \end{array} \quad (Ia)$$

or $$\begin{array}{c} R^3-CH-S-R^1 \\ | \\ R^3-CH-S- \end{array} \quad (IIa)$$

in which $R^1$ and $R^2$, which can be the same or different, represent alkyl radicals, $R^3$ represents an alkyl radical and A represents a divalent radical chosen from among the radicals of formula:

$$-(CH_2)_m-$$

$$-(CH_2)_n-X-(CH_2)_p,$$

$$\begin{array}{c} -CH- \\ | \\ R^3 \end{array}$$

in which m is equal to 0 or is an integer from 1 to 6, n and p are integers from 1 to 6 and X represents O or S, in order to complex the palladium with the said extractant and b) separating the palladium-depleted aqueous solution from the palladium complex formed in stage a).

The alkyl radicals used in the invention for $R^1$, $R^2$ and $R^3$ can be straight or branched radicals. They preferably have 4 to 18 carbon atoms in order to give the ligand a high lipophilicity, which aids palladium extraction.

Particularly interesting examples of thioether ligands are the following compounds:

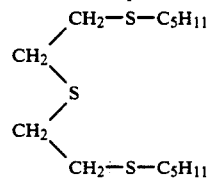

6,9,12-trithiaheptadecane:  Compound 1

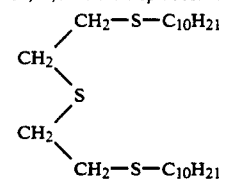

11,14,17-trithiaheptacosane:  Compound 2

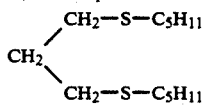

6,10-dithiapentadecane:  Compound 3

The thioether ligands according to the invention can be prepared by conventional processes from the corresponding sodium dithiolates of formula $NaSCH_2ACH_2SNa$ or formula:

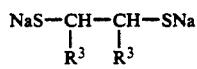

which is reacted with halogen derivatives of formula $R^1X$ and $R^2X$, in which $R^1$ and $R^2$ have the meanings given hereinbefore and X is a halogen atom. This corresponds to the following reaction diagram:

$$\begin{array}{ccc} \text{CH}_2\text{—SNa} & & \text{CH}_2\text{—SR}^1 \\ | & & | \\ \text{A} & + \text{R}^1\text{X} + \text{R}^2\text{X} \longrightarrow \text{A} & + 2\text{XNa} \\ | & & | \\ \text{CH}_2\text{—SNa} & & \text{CH}_2\text{—SR}^2 \end{array}$$

This reaction can be carried out in a mixture of ethanol and sodium ethanolate. The halogen derivative used is preferably the bromide.

In general, $R^1$ and $R^2$ represent the same alkyl radical and it is not necessary to separate the reaction products.

The starting dithiols are commercially available products or can be prepared from commercial products by conventional methods.

According to the invention, the thioether used for the separation of the palladium can either be in a liquid phase immiscible with the aqueous solution, or fixed to a solid phase.

According to a first embodiment of the inventive process, the thioether is dissolved or diluted in an organic solvent and the aqueous solution containing the palladium is contacted with the organic solvent containing the thioether and then the palladium-depleted aqueous solution is separated from the organic solvent containing the palladium complex.

The organic diluent or solvent used can be chosen e.g. from among chlorinated solvents such as $CHCl_3$, $CH_2Cl_2$, $CCl_3CH_3$, $CHCl_2CHCl_2$, $ClCH_2CH_2Cl$ and dichlorobenzene, ether, hydrocarbons such as heptane, dodecane, benzene and alkylbenzenes, as well as benzonitrile.

The thioether concentration of the organic solvent can vary within a wide range and is in particular dependent on the organic diluent or solvent used.

Thus, the said concentration must be such that a homogeneous organic solution is obtained without crystallization of the thioether or the thioether-Pd complexes. In general, use is made of a thioether concentration between 0.5 and 25% (wt/vol).

When the ligand is liquid and sufficiently lipophilic to be insoluble in the aqueous phase, the latter can be used without solvent.

In this first embodiment of the inventive process, the contacting of the two liquid phases and their separation can be carried out in conventional equipment, e.g. countercurrent or cocurrent exchange columns, such as pulsed columns or in mixer-settler means. Normally working takes place at ambient temperature and pressure.

Generally, the aqueous starting solution has a nitric acid concentration of 0.1 to 5 mole/l. It is then possible to reextract the palladium in an aqueous solution, e.g. water.

According to a second embodiment of the inventive process, the thioether ligand is supported by a solid phase. In this case, contacting takes place between the aqueous solution containing the palladium and the solid phase supporting the thioether and the palladium-depleted aqueous solution is separated from the solid phase incorporating the palladium complex.

The solid phases which can be used are e.g. organic or mineral phases grafted with the unit $$\begin{array}{ccc} \text{CH}_2\text{—S—} & & \text{R}^3\text{—CH—S—} \\ | & & | \\ \text{A} & \text{or} & \\ | & & | \\ \text{CH}_2\text{—S—R}^1 & & \text{R}^3\text{—CH—S—R}^1 \end{array}$$

For example, the organic phases which can be used can in particular be polymers of styrene derivatives such as polymethyl styrene having on its methyl groups the radical of formula Ia or IIa. This solid phase can be prepared by reacting polychloromethyl styrene with a thiol of formula:

$$\begin{array}{ccc} \text{CH}_2\text{—SH} & & \text{R}^3\text{—CH—SH} \\ | & & | \\ \text{A} & \text{or} & \\ | & & | \\ \text{CH}_2\text{—SH} & & \text{R}^3\text{—CH—SH} \end{array}$$

in an organic solvent, in the presence of an alkyl iodide, which corresponds to the following reaction diagram:

[reaction diagram showing polychloromethyl styrene reacting with dithiol in solvent/$R^1I$ to give the grafted polymer with $-CH_2-S-CH_2-A-CH_2-SR^1$ substituent]

As has been shown hereinbefore, the process according to the invention is more particularly applied to the recovery of the palladium present in nitric aqueous solutions resulting from the reprocessing of irradiated nuclear fuels, e.g. aqueous solutions for dissolving irradiated nuclear fuel elements.

BRIEF DESCRIPTION OF THE DRAWINGS

Other features and advantages of the invention can be gathered from the following non-limitative examples and with reference to the attached drawings, wherein show.

Figure 1:
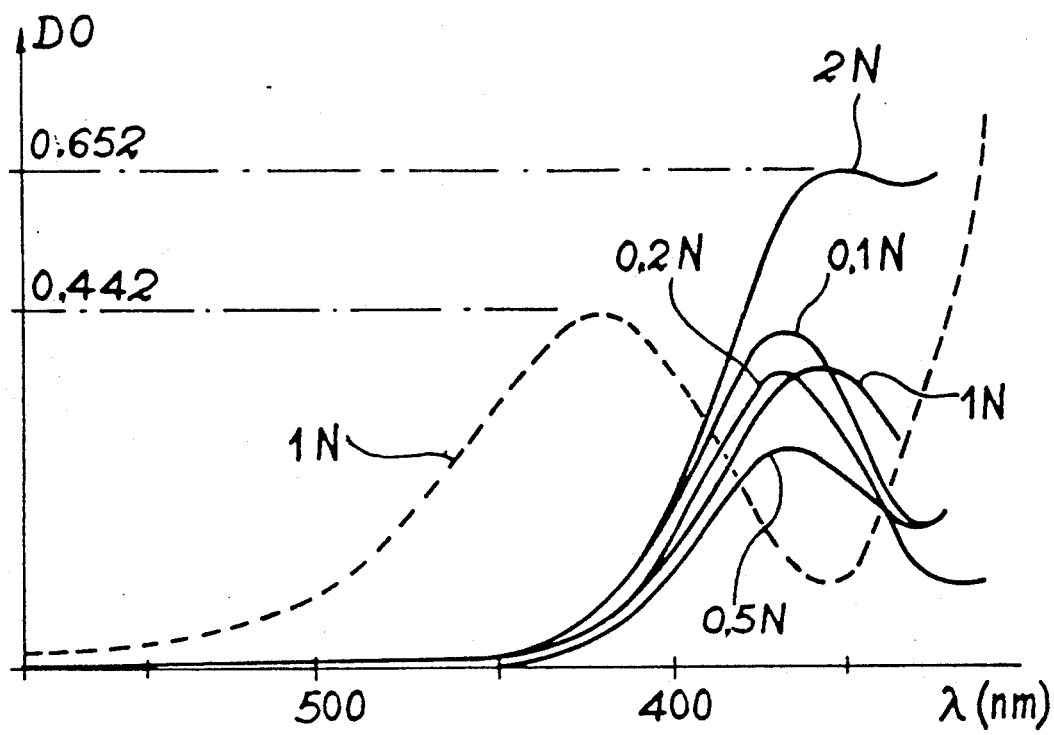
FIG. 1 the UV/visible spectra on nitric aqueous solutions following the extraction of palladium by the process according to the invention.

EXAMPLE 1: PREPARATION OF 6,9,12-TRITHIAHEPTADECANE (Compound 1) of formula:

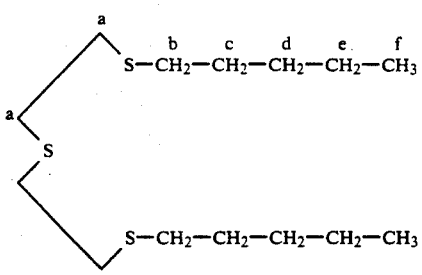

150 ml of absolute ethanol are introduced into a 500 ml three-necked flask, under argon, which is equipped with a thermometer, a condenser and a dropping funnel. Into it are dissolved 4.6 g of sodium (0.20 mole) and heating takes place to 45° C. This is followed by the slow addition of 15.43 g of an ethanolic 3-thia-1,5-pentane dithiol solution (0.10 mole). After stirring for 30 min., slow addition takes place of 25.58 g of an ethanolic 1-chloropentane solution (0.24 mole) and refluxing takes place for 4 hours. The reaction mixture is brought to ambient temperature, followed by filtering. This gives 28.8 g of crude product which is solubilized in 200 ml of dichloromethane and this is all washed with 2×100 ml of distilled water. Drying takes place on MgSO$_4$, followed by filtration. After evaporating the solvent, recrystallization takes place twice in ethanol giving 18.21 g of 6,9,12-trithiaheptadecane, which corresponds to a 62% yield. The said thioether has the following characteristics:

melting point: <50° C.

$^1$H NMR 200 MHz (CDCl$_3$): δ2.75 (m, 8Ha), 2.55 (t, 4Hb), 1.60 (q, 4Hc), 1.35 (m, 4Hd and 4He), 0.90 (t, 6Hf).

EXAMPLE 2: PREPARATION OF 11,14,17-TRITHIAHEPTACOSANE (Compound 2) of formula:

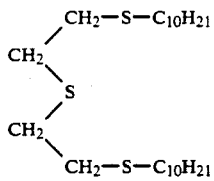  Compound No. 2

The same operating procedure as in Example 1 is adopted for preparing compound 2, except that use is made of 42.42 g of 1-chlorodecane (0.24 mole) instead of 25.58 g of 1-chloropentane. Compound 2 is obtained with a 96% yield.

EXAMPLE 3: PREPARATION OF 6,10-DITHIAPENTADECANE (Compound 3) of formula:

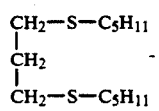

The same operating procedure as in Example 1 is used for preparing compound 3, except that use is made of 10.8 g of 1,3-propane dithiol (0.10 mole) in place of 15.43 g of 3-thiapentane-1,5-dithiol. Compound 3 is obtained with a 73% yield.

EXAMPLE 4

This example uses compound 1 of Example 1, i.e. 6,9,12-trithiaheptadecane in a chloroformic solution incorporating 1% (wt/vol) of compound 1 for extracting the palladium from a nitric solution.

1 ml of a palladium chloride solution PdCl$_2$ having 0.4 g/l (2.25.10$^{-3}$ mole/l) in 1N nitric acid, with 1 ml of a chloroformic solution containing 1% (wt/vol) of compound 1. After stirring for 5 min., the two phases are allowed to settle and it is noted that both phases are coloured, whereas initially only the aqueous solution containing the palladium salt was coloured.

Thus, the chloroformic solution of compound 1 makes it possible to extract the palladium present in the aqueous solution.

EXAMPLE 5

This example makes use of compound 2 and the same operating procedure as in Example 4 is used for extracting the palladium from the same nitric aqueous solution using a 1% (wt/vol) chloroformic solution of compound 2 of Example 2.

After settling, the colouring is distributed over the two phases, which demonstrates that the palladium has been extracted from the organic phase.

EXAMPLE 6

This example uses compound 3 of Example 3 and the operating procedure of Example 4 is used for extracting the palladium from the same aqueous solution. After settling the two phases, it can be seen that both of them are coloured, which shows that the palladium has been extracted from the organic phase.

COMPARATIVE EXAMPLE 1

This example uses 6,9-dithiatetradecane, i.e. the compound of formula:

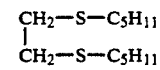

for extracting the palladium from the same nitric aqueous solution as that of Examples 4 to 6. The same operating procedure is followed, but in this case following the settling of the two phases it can be see that only the aqueous phase is coloured. Therefore the palladium is not extracted by this thioether, because the latter does not have a high lipophilicity in the manner of those used in Examples 4,5 and 6.

EXAMPLES 7 to 12

These examples are used for evaluating the selectivity for the extraction of palladium of the thioether (compound 1) used in Example 4, adopting the same operating procedure as in Example 4 using other coloured nitric solutions of metal salts. A visual evaluation takes place of the degree of extraction, as in Example 4, after stirring for 5 min. and after 48 h.

The composition of the aqueous starting solutions and the results obtained are given in table 1.

TABLE 1

| Ex. | Aqueous starting solution | Extraction after 5 min. | after 48 h |
|---|---|---|---|
| 4 | $PdCl_2$ 0.4 g $l^{-1}$, 1N $HNO_3$ | yes | yes |
| 7 | $UO_2(NO_3)_2$ 250 g $l^{-1}$, 1N $HNO_3$ | no | no |
| 8 | $HAuCl_4$, 1N $HNO_3$ | no | no |
| 9 | $FeCl_3$, 1N $HNO_3$ | no | no |
| 10 | $CuCl_2$, 1N $HNO_3$ | no | no |
| 11 | $NiCl_2$, 1N $HNO_3$ | no | no |
| 12 | $RuCl_3$, 1N $HNO_3$ | no | no |

These results make it clear that all the other metals and in particular uranium are not extracted by this thioether. Thus, this ligand permits the extraction of the palladium, but has no affinity for the iron, copper, nickel, ruthenium and in particular uranium salts.

EXAMPLES 13 TO 18

In these examples a study is made of the influence of the nitric acid concentration of the aqueous starting solution on palladium extraction.

In all cases, contacting takes place of 5 ml of nitric aqueous solution containing 0.4 g/l (i.e. 2.25 mole/l of $PdCl_2$) with 5 ml of a solution of the ligand of Example 1 and having a concentration of 10 g/l in chloroform. The two solutions are mixed for 1 min. and are then allowed to settle for 30 minutes. The optical density of the organic and aqueous phases is then determined by UV/visible spectrometry.

The UV/visible spectra of the aqueous solution prior to extraction have a maximum at 420 nm, whereas after extraction these solutions have a maximum at 370 nm. The maximum at 370 nm can be attributed to the presence of palladium complexed only in the form ($Pd^{2+}$ (compound 1) $(NO_3)_2$), because the same spectrum type is obtained by saturating a $Pd^{2+}$ solution having 0.04 g/l in 0.1N nitric acid with crystals of compound 1 used in this example.

Table 2 gives the wavelengths $\lambda$max corresponding to the absorption maximum of the aqueous solutions, before and after extraction, as well as the optical densities OD corresponding to the maximum wavelength $\lambda$max, before and after extraction.

TABLE 2

| Example | 13 | 14 | 15 | 16 | 17 |
|---|---|---|---|---|---|
| $(HNO_3)$ in mole.$l^{-1}$ | 0.1 | 0.2 | 0.5 | 1.0 | 2.0 |
| $\lambda$max (nm) before extraction | 420 | 420 | 420 | 420 | 420 |
| OD $\lambda$max before extraction | 0.482 | 0.433 | 0.450 | 0.442 | 0.471 |
| $\lambda$max (nm) after extraction | 370 | 370 | 370 | 360 | 350 |
| OD $\lambda$max after extraction | 0.446 | 0.386 | 0.285 | 0.388 | 0.652 |

FIG. 1 shows the visible UV spectra of aqueous solutions after extraction. The dotted line curve relates to the 1N aqueous solution before extraction.

The displacement of the absorption maximum and the increase thereof for nitric acid concentrations above 0.5N can be explained by the fact that the solubility in the aqueous solution of the thioether ligand and/or the corresponding complex increases with the acidity of said solution.

On the basis of the results obtained in Examples 13 to 17, it is possible to calculate the partition coefficients of the palladium for relatively low $HNO_3$ concentrations and then calculate the extraction constant. The partition coefficients of the palladium $D_{Pd}$ corresponding to the ratio of the concentration in Pd of the organic phase $(Pd)_O$ on the palladium concentration $(Pd)_a$ of the aqueous phase are given in the following table 3.

TABLE 3

| Example | 13 | 14 | 15 |
|---|---|---|---|
| $(HNO_3)$ (mole/l) | 0.1 | 0.2 | 0.5 |
| OD observed in aqueous phase | 0.446 | 0.386 | 0.285 |
| $D_{Pd}$ | 20.83 | 24.4 | 32.25 |

These results make it clear that there is a very high partition coefficient.

It is possible to calculate the extraction constants starting with the optical densities observed in the organic phase, before and after extraction and comparing the optical densities obtained for the initial 0.1N and >0.5N nitric acid concentrations. For the latter, it is considered that the palladium is totally extracted, which makes it possible to determine the molecular extinction coefficient of the complex and consequently the partition coefficient and extraction constant of the palladium, in accordance with the formula:

$$K_{ex} = \frac{(PdL(NO_3)_2)_0}{(Pd)(NO_3)^2(L)_0}$$

in which L represents the thioether ligand, assuming that the ligand concentration in equilibrium is close to the initial ligand concentration.

The results obtained in the case of Example 13 are given in the following Table 4.

TABLE 4

| | $\lambda = 440$ nm | $\lambda = 450$ nm |
|---|---|---|
| $D_{Pd}$ | 1.06 | 1.004 |
| $K_{ex}$ (mole$^{-3}$ l$^3$) | 3.4 $10^5$ | 3.24 $10^5$ |

The extraction constants obtained show that this thioether is a particularly effective extractant for palladium.

EXAMPLE 18: PALLADIUM REEXTRACTION

In this example, extraction firstly takes place of the palladium in a chloroformic solution containing 1% (wt/vol) of the thioether (compound 1) of Example 1 on the basis of a 0.1N nitric solution containing $2.25.10^{-3}$ mole/l of $PdCl_2$.

Extraction takes place by contacting 5 ml of the aqueous solution with 5 ml of the organic solution, accompanied by stirring for 1 min., and then allowing settling to take place for 30 minutes, in order to recover a palladium-depleted aqueous phase and an organic phase containing the palladium complex.

Figure 2:
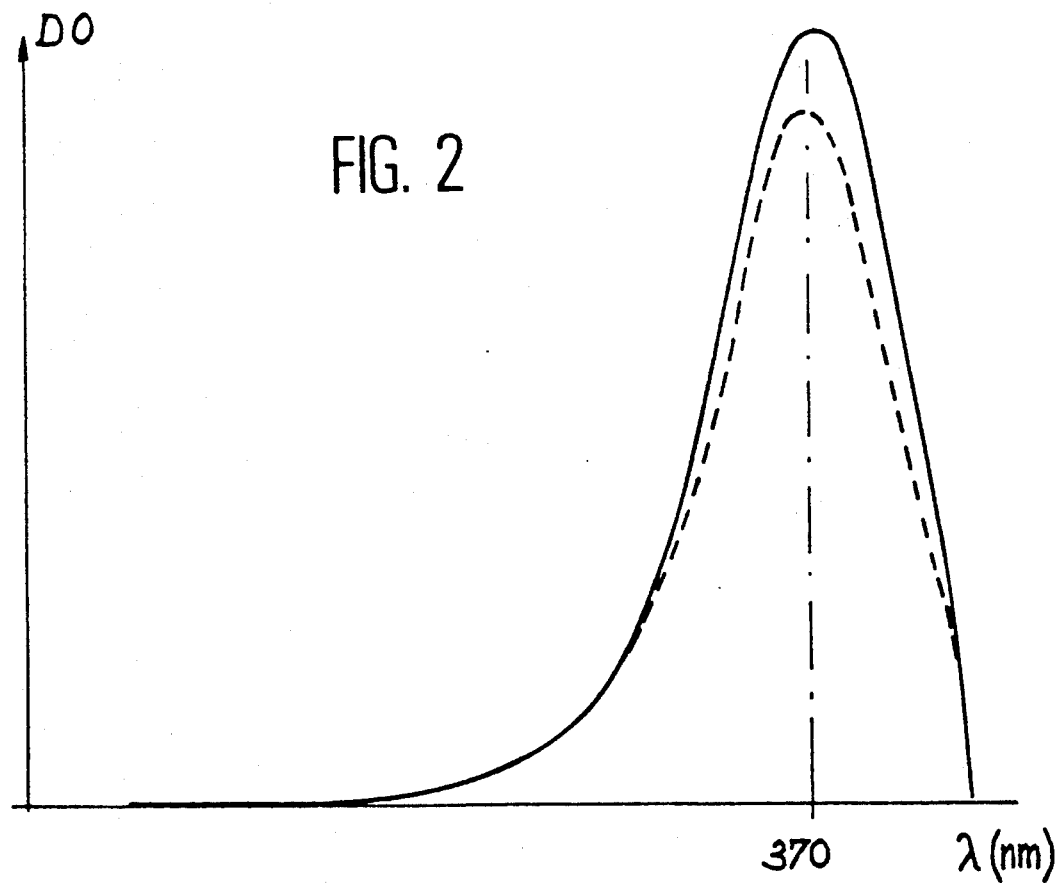
FIG. 2 the UV/visible absorption spectra of $Pd^{2+}$ solutions.

Accompanied by stirring and for 5 min., contacting then takes place of 2 ml of the organic phase separated with 18 ml of $H_2O$ and settling takes place for 2 h. This is followed by the determination of the palladium quantity reextracted in water by measuring the optical density in UV/visible. The UV/visible spectrum obtained is given in FIG. 2. The latter also shows in dotted line form the UV/visible spectrum of a $0.225.10^{-3}$ mole/l $PdCl_2$ solution in saturated 0.01N $HNO_3$ of compound 1. The presence of a maximum of 370 nm indicates that it is the complex $PdL(NO_3)_2$, which is reextracted. The optical density measured at this wavelength makes it possible to determine the efficiency of the extraction-reextraction operation.

$$Y\% = \frac{OD^{370}_{reextracted} \times 9}{OD^{370}_{0.225 \cdot 10^{-3} mole \cdot 1^{-1}} \times 10} \approx 100\%$$

Thus, the extraction and reextraction by water of the palladium can be carried out quantitatively using compound 1.

EXAMPLE 19

This example uses the thioether ligand (compound 1) of Example 1 for extracting the palladium from an aqueous solution containing palladium and uranium and having the following composition:
$HNO_3$: 1N.
$PdCl_2$: 0.4 g/l (2.25.10$^{-3}$ mole/l).
$UO_2^{2+}$: 250 g/l.

In this example contacting takes place of 5 ml of aqueous solution and 5 ml of a chloroformic solution containing 1% (wt/vol) of compound 1 of Example 1. Stirring takes place for 1 min. and then settling takes place for 30 min. This is followed by the separation of the aqueous phase from the organic phase and then 2 ml of the organic phase is contacted with 18 ml of water for 5 min., followed by settling for 2 h. The aqueous phase is then separated and its optical density measured by UV/visible spectrometry. The UV/visible spectrum of the aqueous reextraction solution has the same characteristics as that obtained in the previous example. Thus, it has an absorption maximum at 370 nm and little or no absorption due to the uranyl nitrate. On the basis of the optical density observed at 370 nm, it is possible to determine the efficiency of the extraction and reextraction operation (Y), which is equal to 99.5%.

Thus, the presence of a large amount of uranyl nitrate is only very slightly prejudicial to the efficiency of extraction by compound 1 and has little or no detrimental influence on its selectivity.

EXAMPLE 21

This example makes use of the thioether (compound 1) of Example 1 for extracting the palladium present in an active solution containing uranium, plutonium and fission products and which has the following composition:
$UO_2^{2+}$: 250 g/l (in uranium).
$Pu^{4+}$: 550 mg/l.
$Pd^{2+}$: 15 to 20 mg/l.
nitric acidity: 0.9N.
activity: 22 Ci/l.

Figure 3:
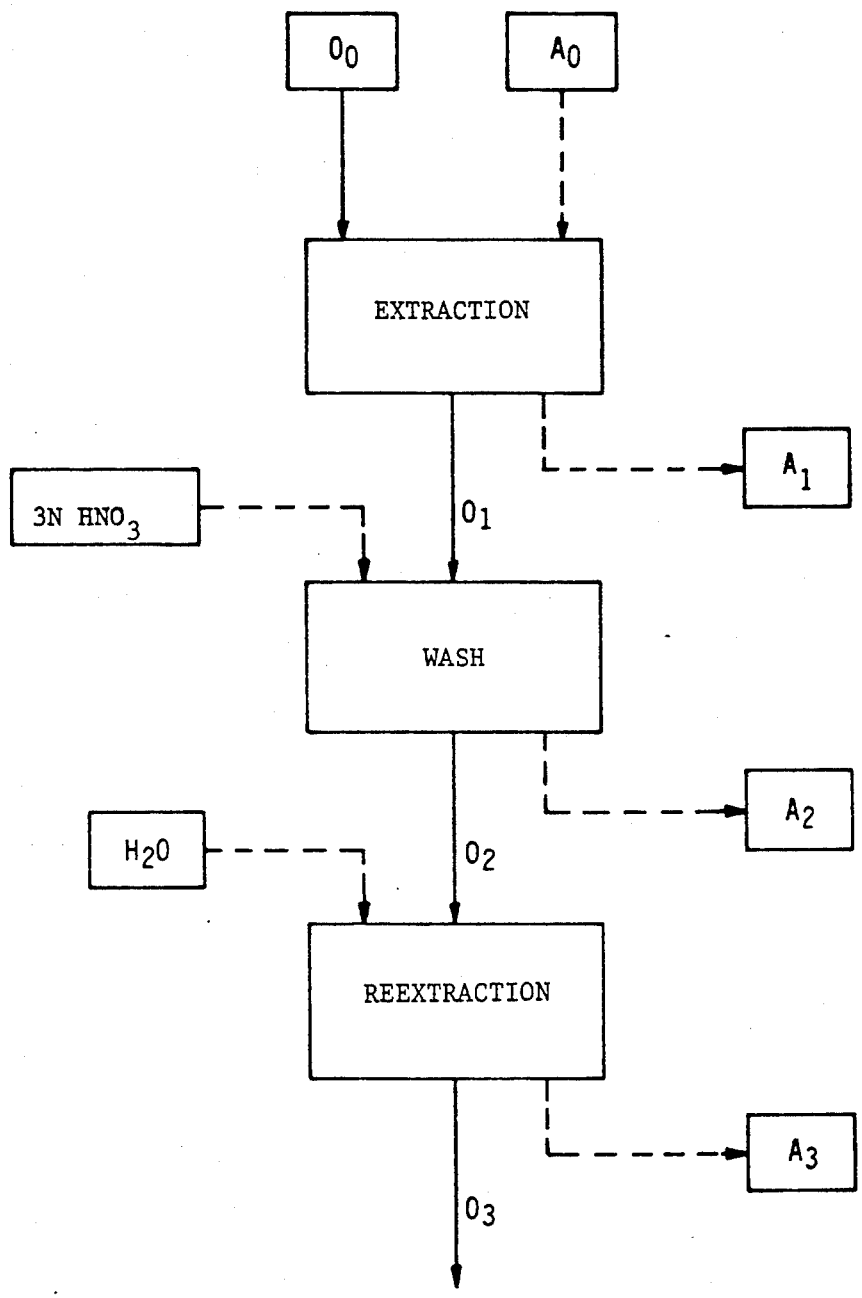
FIG. 3 a diagram showing the performance of the inventive process when applied to the treatment of an irradiated fuel dissolving solution.

The following extraction, washing and reextraction operations are carried out in accordance with the diagram given in FIG. 3.

Thus, contacting takes place between a volume of the aqueous starting solution $A_0$ and a volume of a chloroformic solution $O_0$ containing 1% (wt/vol) of the thioether (compound 1) for 5 min. and then the organic phase $O_1$ is allowed to settle and is separated from the aqueous phase $A_1$. The organic phase $O_1$ is washed with 3N nitric acid and this gives an aqueous phase $A_2$ and an organic phase $O_2$. The palladium present in the organic phase $O_2$ is reextracted by water, which makes it possible to obtain an aqueous reextraction phase $A_3$ and an organic phase $O_3$, which can be recycled in $O_0$.

Determination takes place of the uranium, plutonium and palladium contents, as well as the gamma activity of the aqueous phases obtained after extraction, washing and reextraction. The results obtained are given in table 5.

TABLE 5

| Aqueous phase | U | Pu | Pd | Activity |
| --- | --- | --- | --- | --- |
| A1 | 214 g | 550 mg/l | 0 | 22.3 Ci/l |
| A2 | 25 mg/l | 0.7 mg/l | 2.1 mg/l | 2.5 mCi/l |
| A3 | 5 mg/l | <0.5 mg/l | 13.3 mg/l | 0.74 mCi/l |

The table makes it clear that the palladium is extracted with an excellent yield, the only palladium loss occurring in the aqueous washing solution. However, this loss can be avoided by using more diluted nitric acid in which the thioether-$Pd^{2+}$ complex is less soluble.

Thus, it is possible to recover 70 to 100% of the palladium contained in a solution for dissolving irradiated fuel elements. Therefore the extractants according to the invention make it possible to quantitatively recover the palladium from the dissolving solution of the first cycle with a decontamination factor of 3.10$^4$ following extraction, washing and reextraction.

EXAMPLE 22

In this example the plutonium is extracted by using a solid phase constituted by a resin to which is fixed a radical of formula Ia, in which $R^1$ represents $CH_3$ and A represents $CH_2$.

a) Preparation of the resin incorporating the thioether

In a 50 ml three-necked flask equipped with a condenser, a thermometer and a pouring funnel, reaction takes place of 2.16 g (20 mmole) of HS—$(CH_2)_3$—SH in 14 ml of dimethyl formamide (DMF) with 4.94 g (44 mmole) of potassium butylate and 0.2 g (9.52.10$^{-1}$ mmole) of tetraethyl ammonium bromide. The mixture is left under magnetic stirring for 10 min. and then, using the pouring funnel, introduction takes place of 1.2 ml (20 mmole) of methyl iodide solubilized in 1.5 ml of dimethyl formamide over a period of 1 hour. This is followed by the addition of 2.86 g (2 meq) of polychloromethyl styrene and the mixture is heated to 100° C. for 3 days.

The mixture is allowed to cool to ambient temperature and the resin is washed twice with 10 ml of methanol and twice with 10 ml of soft water. The resin is then placed in 20 ml of dimethyl formamide at reflux at 100° C. for 3 days.

The mixture is cooled to ambient temperature and the resin is washed 5 times with 10 ml of chloroform and then the resin is placed for 24 h in a vacuum dessicator containing $P_2O_5$.

b) Palladium extraction 1 g of the previously synthesized resin incorporating the thioether is suspended in 40 ml of nitric aqueous solution containing 1 mmole/l of palladium and 1.38 mole/l of nitric acid. Magnetic stirring takes place for 1 h. On contact with the resin, the solution, which was initially yellow, loses its colour, whereas the resin becomes a dirty chestnut colour. The resin is then separated from the solution by filtering on filter paper and the palladium content of the nitric solution is determined by atomic absorption.

All the palladium is extracted by the resin, which therefore contains 4.256 mg of palladium per gramme of resin. Thus, the extraction is total, but the palladium mass extracted per gramme of resin is low.

In order to evaluate the selectivity of the resin, the same extraction test is carried out, but using nitric aqueous solutions containing 1 mmole/l of rhodium, nickel, copper or uranium.

At the end of the operation, it is found that the resin contains none of the metals present in the aqueous solutions. Thus, the extraction percentage of rhodium, nickel, copper and uranium by said resin is 0. Therefore the resin has a very good selectivity for palladium.

We claim:

1. Process for separating the palladium present in an aqueous solution it comprises the following stages:

a) contacting the aqueous solution containing the palladium with an organic extractant constituted by a thioether in accordance with the formula:

$$\begin{array}{c} CH_2-S-R^1 \\ | \\ A \\ | \\ CH_2-S-R^2 \end{array} \qquad (I)$$

or $$\begin{array}{c} R^3-CH-S-R^1 \\ | \\ R^3-CH-S-R^2 \end{array} \qquad (II)$$

or incorporating a radical of formula:

$$\begin{array}{c} CH_2-S-R^1 \\ | \\ A \\ | \\ CH_2-S- \end{array} \qquad (Ia)$$

or $$\begin{array}{c} R^3-CH-S-R^1 \\ | \\ R^3-CH-S- \end{array} \qquad (IIa)$$

in which $R^1$ and $R^2$, which can be the same or different, represent alkyl radicals, $R^3$ represents an alkyl radical and A represents a divalent radical chosen from among the radicals of formula:

$$-(CH_2)_m-$$

$$-(CH_2)_n-X-(CH_2)_p-$$

$$\begin{array}{c} -CH- \\ | \\ R^3 \end{array}$$

in which m is equal to 0 or is an integer from 1 to 6, n and p are integers from 1 to 6 and X represents O or S, in order to complex the palladium with the said extractant and b) separating the palladium-depleted aqueous solution from the palladium complex formed in stage a).

2. Process according to claim 1, wherein the thioether is in accordance with formula (I), in which A represents $-CH_2-$ and $R^1$ and $R^2$ represent the pentyl radical.

3. Process according to claim 1, wherein the thioether is in accordance with formula (I), in which A represents $-CH_2-S-CH_2-$ and $R^1$ and $R^2$ represent the pentyl radical.

4. Process according to claim 1, wherein the thioether complies with formula (I), in which A represents $-CH_2-S-CH_2-$ and $R^1$ and $R^2$ represent the decyl radical.

5. Process according to any one of the claims 1 to 4, wherein the thioether is dissolved or diluted in an organic solvent and in that contacting takes place between the aqueous solution containing the palladium and the organic solvent containing the thioether, followed by separation of the palladium-depleted aqueous solution from the organic solvent containing the palladium complex.

6. Process according to any one of the claims 1 to 4, wherein the thioether is supported by a solid phase and in that contacting takes place between the aqueous solution containing the palladium and the solid phase supporting the thioether.

7. Process according to claim 6, wherein the solid phase is polymethyl styrene having on its methyl groups a radical of formula (Ia) or (IIa).

8. Process according to claim 1, wherein the aqueous solution is a nitric aqueous solution resulting from the reprocessing of irradiated nuclear fuels.

9. Process according to claim 8, wherein the nitric aqueous solution is an aqueous solution from dissolving irradiated nuclear fuel elements.

10. Process according to claim 8, wherein the nitric acid concentration of the aqueous solution is 0.1 to 5 mol/l.

11. Process according to claim 5, wherein palladium is then recovered from the organic solvent by reextraction in an aqueous solution.

* * * * *